United States Patent [19]
Tsukada et al.

[11] Patent Number: 5,694,197
[45] Date of Patent: Dec. 2, 1997

[54] CORNEAL SHAPE MEASURING APPARATUS

[75] Inventors: Hisashi Tsukada; Tsutomu Sato; Hideki Hatanaka; Minoru Kamiya; Takeyuki Kato, all of Tokyo, Japan

[73] Assignee: Kabushiki Kaisha Topcon, Tokyo, Japan

[21] Appl. No.: 550,497

[22] Filed: Oct. 30, 1995

[30]  Foreign Application Priority Data

Oct. 28, 1994 [JP] Japan .................................. 6-265283

[51] Int. Cl.$^6$ .................................. A61B 3/14; A61B 3/10
[52] U.S. Cl. .................................. 351/206; 351/212
[58] Field of Search .................................. 351/206, 205, 351/212, 211, 221, 246; 384/62

[56] References Cited

FOREIGN PATENT DOCUMENTS 4126329  3/1992  Germany .................................. 351/206

*Primary Examiner*—Hung X. Dang
*Attorney, Agent, or Firm*—Finnegan, Henderson, Farabow, Garrett & Dunner, L.L.P.

[57]  ABSTRACT

A corneal shape measuring apparatus is provided which measures a corneal shape in such a way that a reflection image from a cornea (15) is recorded as image data and then the image data is analyzed. The apparatus includes LEDs (14) for projecting an index onto a subject's eye in order to detect a position of an apparatus body (3) in up, down, right, and left directions and in forward and backward directions with respect to the eye, an automatic photographic mode in which the eye is automatically photographed when a position of the apparatus body in up, down, right, and left directions with respect to the and a position of the apparatus body in forward and backward directions with respect to the eye are each within a predetermined range, a semi-automatic photographic mode in which the eye is photographed when a position of the apparatus body in up, down, right, and left directions with respect to the eye and a position of the apparatus body in forward and backward directions with respect to the eye are each within the predetermined range and, at the same time, a photography switch (11') is operated, and a manual photographic mode in which the eye is photographed when the photography switch is operated regardless of a position of the apparatus body with respect to the eye. A positional relationship of the apparatus body (3) to the eye is stored correspondingly to recorded image data.

13 Claims, 6 Drawing Sheets

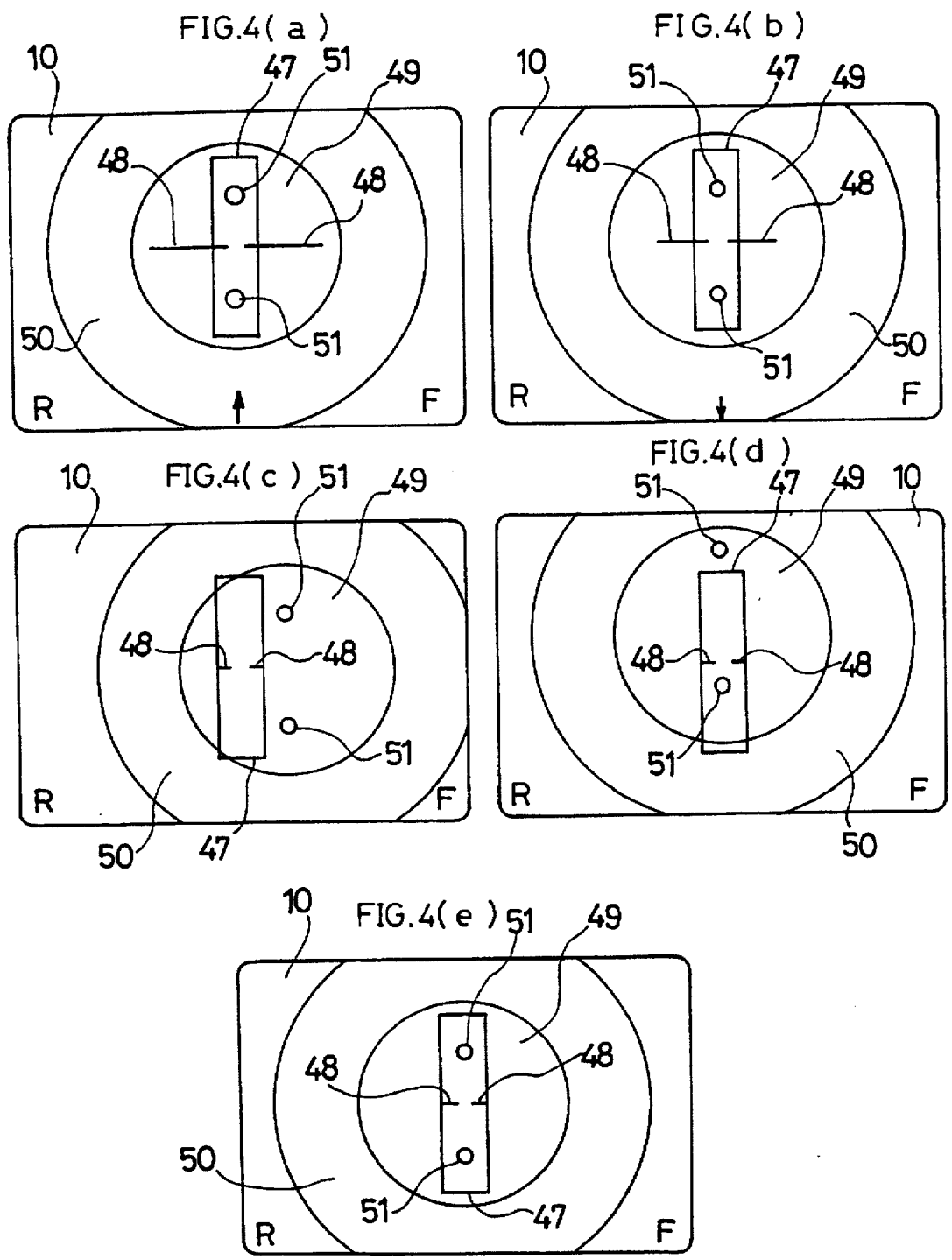

5,694,197

CORNEAL SHAPE MEASURING APPARATUS

BACKGROUND OF THE INVENTION

1. Field of the Invention

This invention relates to improvements in a corneal shape measuring apparatus capable of measuring the shape of a cornea by recording a reflection image, such as a ring image reflected by the cornea, in the form of image data and analyzing the recorded image data.

2. Description of the Prior Art

A corneal shape measuring apparatus is known in which a ring image is projected onto a cornea of a subject's eye and then the ring image as a reflection image reflected by the cornea is received and recorded in a recording means so that the shape of the ring image can be analyzed. If a position of an apparatus body with respect to the subject's eye in up, down, right, and left directions is within a given range, and at the same time, a position of the apparatus body with respect to the subject's eye in forward and backward directions is within a given range, the corneal shape measuring apparatus can automatically take a photograph of the eye.

However, there are cases in which it is difficult to set the position of the instrument body with respect to the subject's eye in up, down, right, and left directions or in forward and backward directions within the given range. For example, such a difficult case arises when a keratoconus is measured or when an infant's eye is examined. It is also difficult to do so when not a human eye but an animal eye is examined.

In this connection, there might be an operator (oculist) desiring to very strictly set the position of the apparatus body with respect to the subject's eye in up, down, right, and left directions and in forward and backward directions within the given range in order to photograph the cornea.

In order to overcome the disadvantage or realize the desire, it is to be desired that the corneal shape measuring apparatus is provided with an automatic photographic mode in which the subject's eye is automatically photographed when a position of the apparatus body with respect to the subject's eye in up, down, right and left directions and a position of the apparatus body with respect to the subject's eye in forward and backward directions are each within a given range, a semi-automatic photographic mode in which the subject's eye is photographed when a position of the apparatus body with respect to the subject's eye in up, down, right, and left directions and a position of the apparatus body with respect to the subject's eye in forward and backward directions are each within the given range and, at the same time, a photographing switch is operated, and a manual photographic mode in which the subject's eye is photographed when the photographing switch is operated regardless of whether the apparatus body with respect to the subject's eye is positioned within the given range or not.

However, the provision of the plurality of photographic modes in the apparatus causes a problem of making it difficult to decide which one of the modes is used to photograph the cornea and obtain image data.

In addition, there is another problem in that it is impossible to judge whether the obtained image data is entirely reliable or not because the image data or analysis data obtained by the conventional apparatus does not indicate a position of the apparatus body with respect to the subject's eye in up, down, right, and left directions and in forward and backward directions.

In addition, in order to minutely examine the subject's eye at periodic intervals and ascertain how the cornea of the identical eye is improving toward full recovery, it is to be desired that the cornea is photographed in such a way that the apparatus body is placed at the same position as the previous position at which the previous photography was carried out.

It is therefore a first object of the present invention to provide a corneal shape measuring apparatus capable of changing a photographic mode to another photographic mode as occasion demands.

It is a second object of the present invention to provide a corneal shape measuring apparatus capable of later ascertaining which one of photographic modes was used to obtain image data.

It is a third object of the present invention to provide a corneal shape measuring apparatus capable of later ascertaining, per image data, a position of an apparatus body with respect to a subject's eye in up, down, right, and left directions and in forward and backward directions.

SUMMARY OF THE INVENTION

In order to achieve the first object, the corneal shape measuring apparatus in which a reflection image reflected by a cornea is recorded in the form of image data to be analyzed for the measurement of the shape of the cornea includes at least two photographic modes of automatic, semi-automatic, and manual photographic modes. Preferably, photographic mode information corresponding to recorded image data is recorded. Thereby, the second object can be achieved.

Further, in order to achieve the first object, the corneal shape measuring apparatus in which a reflection image reflected by a cornea is recorded in the form of image data to be analyzed for the measurement of the shape of the cornea is provide with an automatic photographic mode in which a subject's eye is automatically photographed when a position of an apparatus body in up, down, right, and left directions with respect to the subject's eye is within a predetermined range and a position of the apparatus body in forward and backward directions with respect to the subject's eye is within a predetermined range, a semi-automatic photographic mode in which the subject's eye is photographed when a position of the apparatus body in up, down, right, and left directions with respect to the subject's eye is within a predetermined range and a position of the apparatus body in forward and backward directions with respect to the subject's eye is within a predetermined range and, at the same time, a photography switch is operated, and a manual photographic mode in which the subject's eye is photographed when the photography switch is operated regardless of a position of the apparatus body with respect to the subject's eye. Preferably, photographic mode information corresponding to recorded image data is recorded and displayed together with the image data. By this, the second object is achieved. Further, preferably, the position, determined when the image data is obtained, of the apparatus body in up, down, right, and left directions and in forward and backward directions with respect to the subject's eye is stored correspondingly to the image data or analysis data. By this, the third object is achieved.

In order to achieve the first, second, and third objects, the corneal shape measuring apparatus in which a reflection image reflected by a cornea is recorded in the form of image data to be analyzed for the measurement of the shape of the cornea includes an index projecting means for projecting an index onto a subject's eye in order to detect a position of an apparatus body in up, down, right, and left directions and in forward and backward directions with respect to the subject's eye, an automatic photographic mode in which the subject's eye is automatically photographed when a position of the apparatus body in up, down, right, and left directions with respect to the subject's eye and a position of the apparatus body in forward and backward directions with respect to the subject's eye are each within a predetermined range, a semi-automatic mode in which the subject's eye is photographed when a position of the apparatus body in up, down, right, and left directions with respect to the subject's eye and a position of the apparatus body in forward and backward directions with respect to the subject's eye are each within the predetermined range and, at the same time, a photography switch is operated, and a manual mode in which the subject's eye is photographed when the photography switch is operated regardless of a position of the apparatus body with respect to the subject's eye. A positional relationship of the apparatus body to the subject's eye is stored correspondingly to recorded image data. Preferably, photographic mode information corresponding to the recorded image data is recorded and displayed together with the image data.

According to the present invention, since at least two photographic modes of automatic, semi-automatic, and manual photographic modes are provided in the apparatus, the operator can select one of them as occasion demands.

Further, according to the present invention, in the automatic photographic mode, the subject's eye is automatically photographed when a position of the apparatus body in up, down, right, and left directions with respect to the eye and a position of the apparatus body in forward and backward directions with respect to the eye are each within a predetermined range. In the semi-automatic photographic mode, the eye is photographed when a position of the apparatus body in up, down, right and left directions with respect to the eye and a position of the apparatus body in forward and backward directions with respect to the eye are each within the predetermined range and, at the same time, a photography switch is operated. In the manual photographic mode, the eye is photographed when the photography switch is operated regardless of a position of the apparatus body with respect to the eye.

Further, according to the present invention, a positional relationship of the apparatus body to the eye is stored correspondingly to recorded image data.

BRIEF DESCRIPTION OF THE DRAWINGS

FIGS. 4(a)–4(e) are each a descriptive drawing of a positional relationship between the subject's eye and the apparatus body in automatic photography. In more detail, FIG. 4(a) shows a case where a position of the apparatus body in up, down, right, and left directions with respect to the subject's eye is within an allowable range, but the apparatus body is too away from the eye; FIG. 4(b) shows a case where a position of the apparatus body in up, down, right, and left directions with respect to the subject's eye is within the allowable range, but the apparatus body is too near to the eye; FIG. 4(c) shows a case where a position of the apparatus body in forward, backward, up, and down directions with respect to the subject's eye is within the allowable range, but the apparatus body is displaced leftward; FIG. 4(d) shows a case where a position of the apparatus body in forward, backward, right, and left directions with respect to the subject's eye is within the allowable range, but the apparatus body is displaced downward; and FIG. 4(e) shows a case where a position of the apparatus body in every direction with respect to the subject's eye is within the allowable range.

FIG. 5(a) shows a case where a position of the apparatus body in up, down, right, and left directions with respect to the subject's eye is sufficiently within the allowable range, but a position thereof in forward and backward directions with respect to the subject's eye is barely within the allowable range, and FIG. 5(b) shows a case where a position of the apparatus body in up, down, right, and left directions with respect to the subject's eye is within the allowable range, and the apparatus body in forward and backward directions with respect to the subject's eye is positioned at a proper focusing point.

FIGS. 8(a)–8(b) are each a descriptive drawing of image data and photographic mode information displayed on a TV monitor. In more detail.

DETAILED DESCRIPTION OF THE PREFERRED EMBODIMENT

Figure 1:
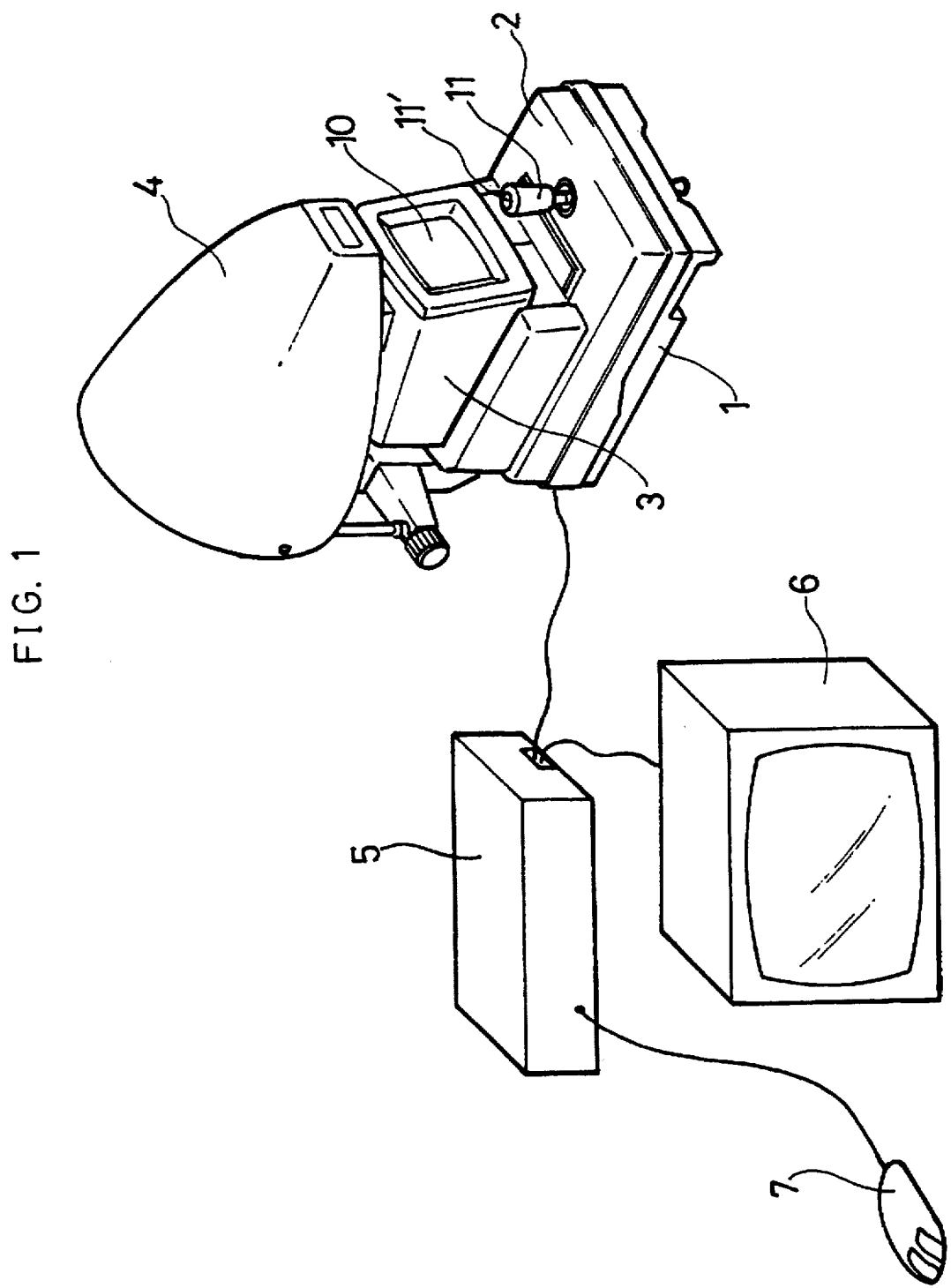
FIG. 1 is a perspective view of the corneal shape measuring apparatus according to the present invention, seen from behind the apparatus.
Figure 2:
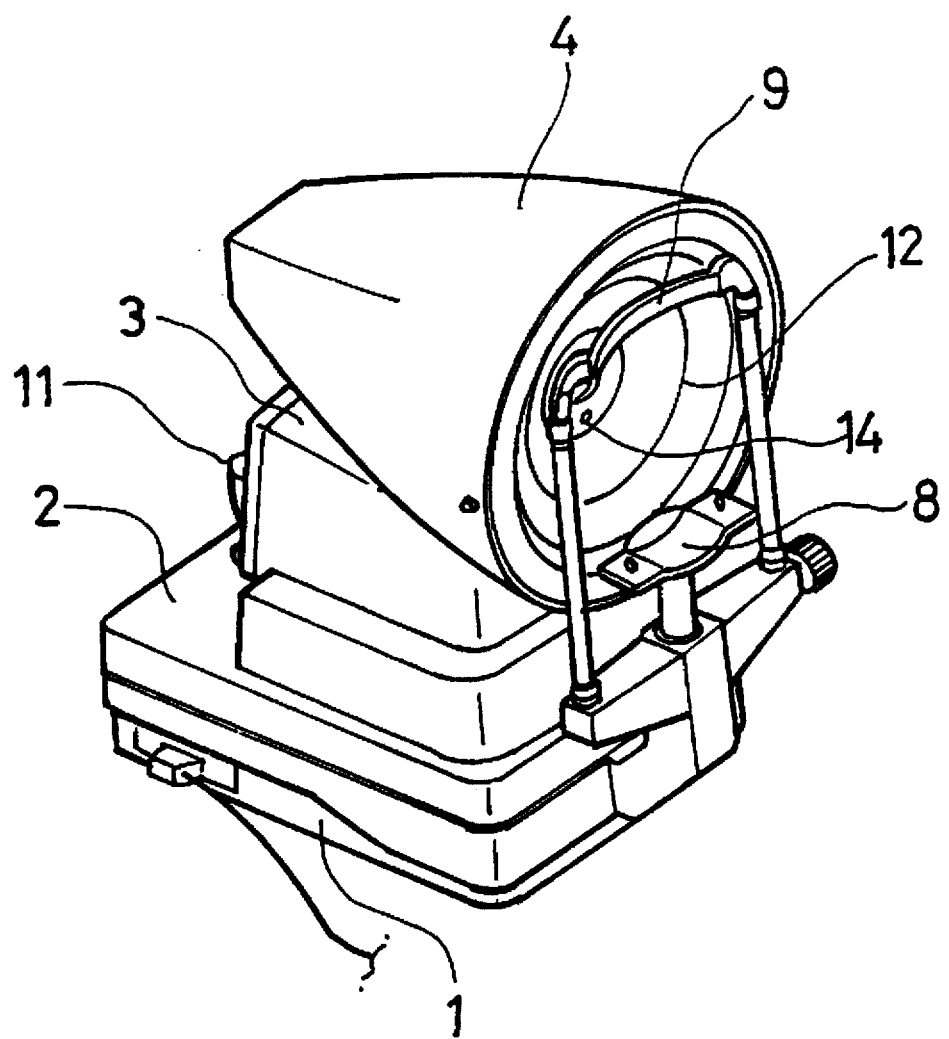
FIG. 2 is a perspective view of the corneal shape measuring apparatus according to the present invention, seen from the front side of the apparatus.

FIGS. 1 and 2 are each a perspective view of a corneal shape measuring apparatus according to the present invention. In FIG. 1, reference numeral 1 designates a base, reference numeral 2 designates a frame, and reference numeral 3 designates an apparatus body. A dome 4 including optical systems is mounted on the apparatus body 3. The apparatus body 3 is connected to a processing unit 5 which is connected to a TV monitor 6. A mouse 7 is connected to the processing unit 5. A chin-rest 8 and a forehead-rest 9 are disposed on the front side of the apparatus body 3 (see FIG. 2). A TV monitor 10 and a control lever 11 are disposed on the rear side of the apparatus body 3. The apparatus body 3 is movable in forward, backward, up, down, right, and left directions with respect to a subject's eye by operating the control lever 11. A photography switch 11' is mounted on the top of the control lever 11.

Figure 3:
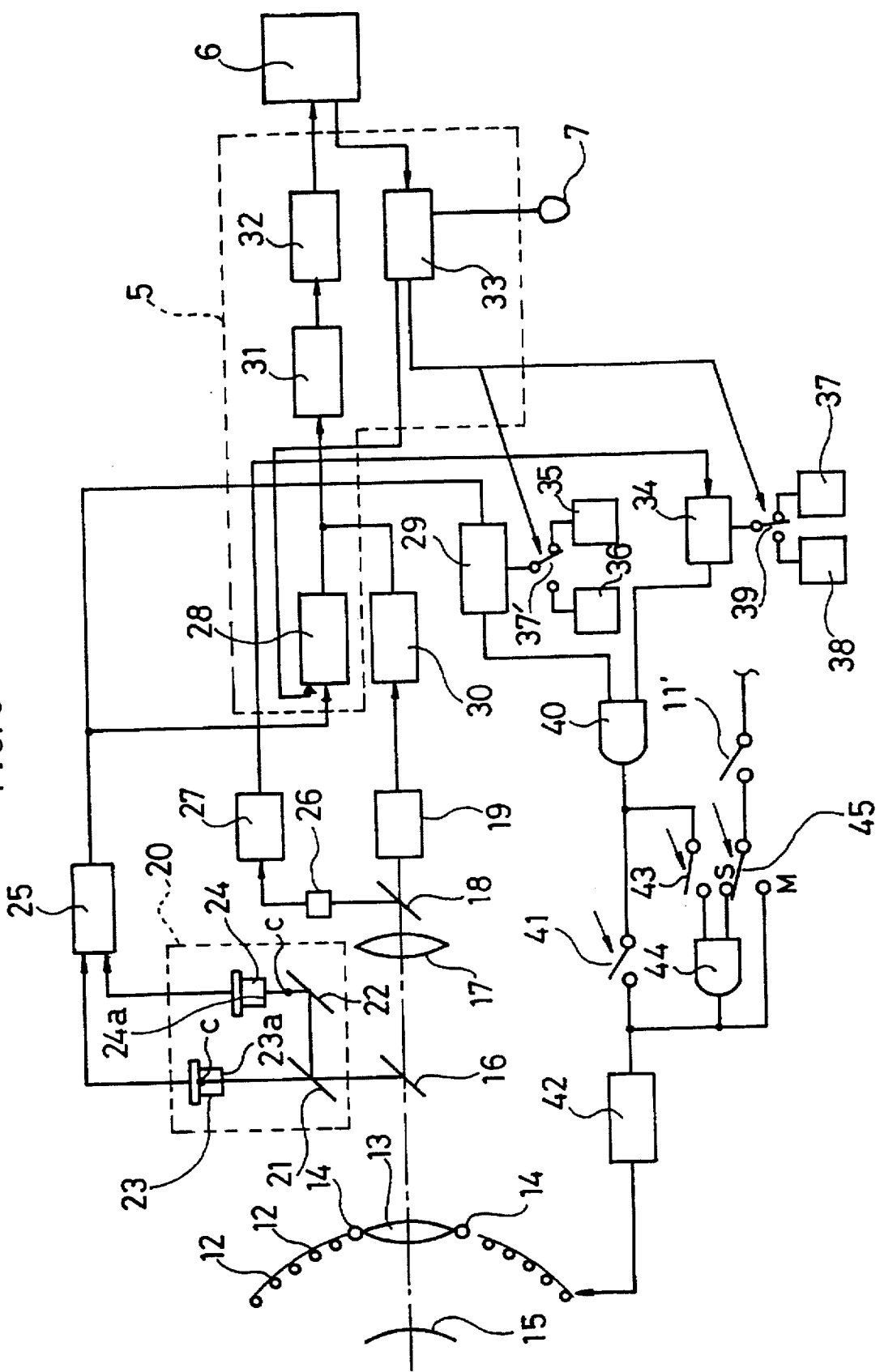
FIG. 3 shows a relationship between processing circuits and optical systems of the corneal shape measuring apparatus according to the present invention.

As shown in FIGS. 2 and 3, concentric ring-like light sources 12 are mounted on the front of the dome 4. An objective lens 13 is disposed at the center of the ring-like light sources 12 concentrically with the light sources 12. With the objective lens 13 between, illumination LEDs 14 serving as light projecting means are disposed on the upper and lower sides of the objective lens 13. The LED 14 projects an index image onto a cornea 15 of a subject's eye. A ring image reflected by the cornea 15 is guided to a CCD camera 19 through the objective lens 13, a half mirror 16, an image formation lens 17, and a half mirror 18. The ring image is imaged on the CCD camera 19. An index image reflected by the cornea 15 passes through the objective lens 13 and reaches the half mirror 16. Part of the index image is reflected by the half mirror 16 and guided to a focus detection sensor 20 which comprises half mirrors 21, 22, and light receiving elements 23, 25. A light receiving surface 23a of the light receiving element 23 is positioned before a focal point C with respect to the cornea 15. A light receiving surface 24a of the light receiving element 24 is positioned after a focal point C with respect to the cornea 15. This is a well known arrangement. Outputs of the light receiving elements 23, 24 are input to an arithmetic circuit 25. Based on the outputs of the light receiving elements 23, 24, the arithmetic circuit 25 judges whether the apparatus body 3 is located before or after the focal point C with respect to the cornea 16 and then a difference from the focal point C is output. The other part of the index image passes through the half mirror 16 and then part of the other part of the index image is reflected by the half mirror 18. The reflected index image is guided to a PSD sensor 26. The remaining index image which has passed through the half mirror 18 is received by the CCD camera 19. The output of the PSD sensor 26 is input to an arithmetic circuit 27. Based on the output of the PSD sensor 26, the arithmetic circuit 27 calculates a position of the apparatus body 3 in up, down, right, and left directions with respect to the cornea 15.

The output of the arithmetic circuit 25 is input to a pattern generator 28 and a comparison circuit 29. The output of the CCD camera 19 is input to a frame memory 30. The outputs of the pattern generator 28 and the frame memory 30 are input to an analysis portion 32 via an image synthesizing device 31. The processing unit 5 includes a photographic mode selecting portion 33 for selecting an automatic photographic mode, a semi-automatic photographic mode, or a manual photographic mode. The selection of any one from the photographic modes is made through the operation of the mouse 7. In the automatic photographic mode, the subject's eye is automatically photographed when a position of the apparatus body 3 with respect to the subject's eye in up, down, right, and left directions and a position of the apparatus body 3 with respect to the subject's eye in forward and backward directions are each within a given range. In the semi-automatic photographic mode, the subject's eye is photographed when a position of the apparatus body 3 with respect to the subject's eye in up, down, right, and left directions and a position of the apparatus body 3 with respect to the subject's eye in forward and backward directions are each within the given range and, at the same time, the photography switch 11' is operated. In the manual photographic mode, the subject's eye is photographed when the photography switch 11' is operated regardless of whether a position of the apparatus body 3 with respect to the subject's eye is within the given range or not.

The output of the arithmetic circuit 27 is input to a comparison circuit 34. The comparison circuit 29 can be connected to a reference value circuit 35 corresponding to the automatic photographic mode or to a reference value circuit 36 corresponding to the semi-automatic photographic mode via a change-over switch 37'. The comparison circuit 34 can be connected to a reference value circuit 37 corresponding to the automatic photographic mode or to a reference value circuit 38 corresponding to the semi-automatic photographic mode via a change-over switch 39. In FIG. 3, the change-over switches 37', 39 are connected to the reference value circuits 35, 37 corresponding to the automatic photographic mode, respectively. The photographic mode selecting portion 33 controls the change-over switches 37', 39 and the pattern generator 28. When the semi-automatic photographic mode is selected by clicking the mouse 7, the change-over switches 37', 39 are connected to the reference value circuits 36, 18, respectively. The outputs of the comparison circuits 29, 34 are input to terminals of an AND circuit 40, respectively. The output of the AND circuit 40 is input to an emission light control circuit 42 via a change-over switch 41 and, at the same time, is input to a terminal of an AND circuit 44 via a change-over switch 43. The photography switch 11' can be connected to the other terminal S of the AND circuit 44 or to a manual terminal M via a change-over switch 45. When the automatic photographic mode is selected, the photographic mode selecting portion 33 turns on the change-over switch 41 and, at the same time, turns off the change-over switch 43. When the semi-automatic photographic mode is selected, the photographic mode selecting portion 33 turns off the change-over switch 41 and turns on the change-over switch 43 and, at the same time, connects the change-over switch 45 to the terminal S of the AND circuit 44. When the manual photographic mode is selected, the photographic mode selecting portion 33 turns off the change-over switches 41, 43 and connects the change-over switch 45 to the manual terminal M. Accordingly, in the manual photographic mode, the subject's eye is photographed by operating the photography switch 11' regardless of the position of the apparatus body with respect to the subject's eye.

As shown in FIGS. 4(a)–4(e), the pattern generator 28 generates a rectangular frame 47 and a focusing line (alignment focus bar) 48 in accordance with mode information obtained by the photographic mode selecting portion 33. In FIGS. 4(a)–4(e), reference numeral 49 designates the pupil of the subject's eye, reference numeral 50 designates the iris thereof, and reference numeral 51 designates an index image (alignment spot) corresponding to each of the LEDs 14. FIGS. 4(a)–4(e) each show a positional relationship in the automatic photographic mode. In FIG. 4(a), a coincidence is brought about between the apex of the cornea 15 of the subject's eye and an optical axis of an optical system of the apparatus body 3. But, the position of the apparatus body 3 in forward and backward directions with respect to the subject's eye is out of an allowable range. This fact is indicated by the focusing line 48 going beyond the rectangular frame 47. On the lower part of the TV monitor 10, an upward arrow is displayed which indicates a direction in which the apparatus body 3 is to be moved. In order to take the focus in this case, the apparatus body 3 is brought close to the subject's eye. In FIG. 4(b), the apex of the cornea 15 of the subject's eye is coincident with the optical axis of the optical system of the apparatus body 3, but the apparatus body 3 is too close to the eye. A downward arrow displayed on the lower part of the TV monitor 10 indicates a direction in which the apparatus body 3 is to be moved. In order to take the focus, the apparatus body 3 is caused to go away from the subject's eye. As a difference between a position of the apparatus body 3 with respect to the subject's eye and a proper focal point becomes closer to an allowable range, a length of the focusing line 48 displayed on the TV monitor 10 becomes shorter. In FIG. 4(c), a position of the apparatus body 3 in the forward and backward directions with respect to the subject's eye is within the allowable range, but the index images 51 are beyond the rectangular frame 47 rightward. This indicates that the optical axis of the optical system of the apparatus body 3 has been deviated from the apex of the cornea 15 leftward. In FIG. 4(d), a position of the apparatus body 3 in forward and backward directions with respect to the subject's eye is within the allowable range, but the index images 51 are displaced upward and, as a result, one of the index images 51 is beyond the rectangular frame 47. This indicates that the optical axis of the optical system of the apparatus body 3 has been deviated from the apex of the cornea 15 downward. If a ring image used as image data is obtained by taking a photograph of the eye in such a state as shown in FIGS. 4(a)–4(d), the quality of reliability of the resultant image data is inferior to that obtained when a position of the apparatus body 3 in forward and backward directions with respect to the subject's eye is within a proper range and when a position of the apparatus body 3 in up, down, right, and left directions with respect to the subject's eye is within a proper range. However, in the automatic photographic mode, the AND circuit 40 is kept low in any state of FIGS. 4(a)–4(d) and therefore the ring-like light sources 12 do not emit light. Accordingly, a ring image is not formed. FIG. 4(e) shows a state in which the index images 51 are within the rectangular frame 47 and, in addition, the focusing lines 48 are within the same 47. When the state shown in FIG. 4(d) is brought about, since the outputs of the comparison circuits 29, 34 each exceed a reference level, the AND circuit 40 becomes high and therefore the light sources 12 emit light. Accordingly, a ring image is formed and recorded. If the states of FIGS. 4(a)–4(d) are displayed on the TV monitor 10 in the automatic photographic mode, the operator (oculist) operates the control lever 11 to move the apparatus body 3 in forward, backward, up, down, right, and left directions in order to bring about the state of FIG. 4(e).

Figure 5A:
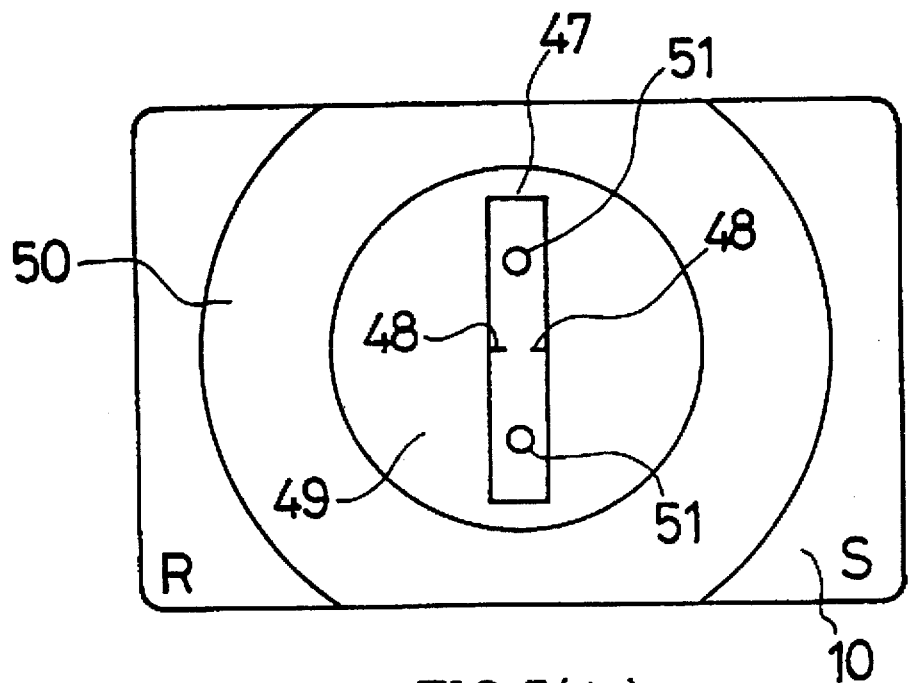
FIGS. 5(a)–5(b) are each a descriptive drawing of a positional relationship between the subject's eye and the apparatus body in semi-automatic photography. In more detail.
Figure 5B:
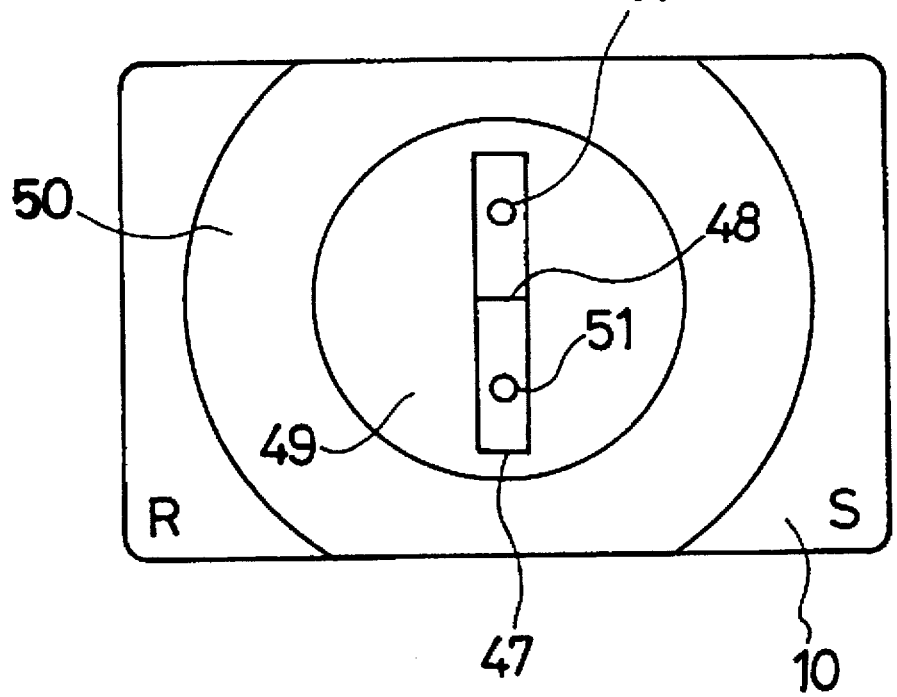

FIGS. 5(a) and 5(b) each show a display state in the semi-automatic photographic mode. In the semi-automatic photographic mode, the lateral width of the rectangular frame 47 displayed on the TV monitor 10 is narrower than that displayed thereon in the automatic photographic mode. A lateral width of the rectangular frame 47 is determined in accordance with a focusing allowable range. The focusing allowable range in the semi-automatic photographic mode is narrower than that in the automatic photographic mode. Further, the allowable range of the apparatus body 3 in lateral directions with respect to the subject's eye in the semi-automatic photographic mode is narrower than that in the automatic photographic mode. Accordingly, the quality of image data obtained in the semi-automatic photographic mode is superior to that obtained in the automatic photographic mode. In the semi-automatic photographic mode, if the photography switch 11' is pushed at the moment when the focusing lines 48 enter the rectangular frame 47 as shown in FIG. 5(a), image data is obtained which is data on the eye photographed when barely within the focusing allowable range. If the photography switch 11' is pushed when the right and left-hand focusing lines 48 are joined to each other as shown in FIG. 5(b), image data is obtained which is data on the eye photographed when at the proper focal point.

Figure 6A:
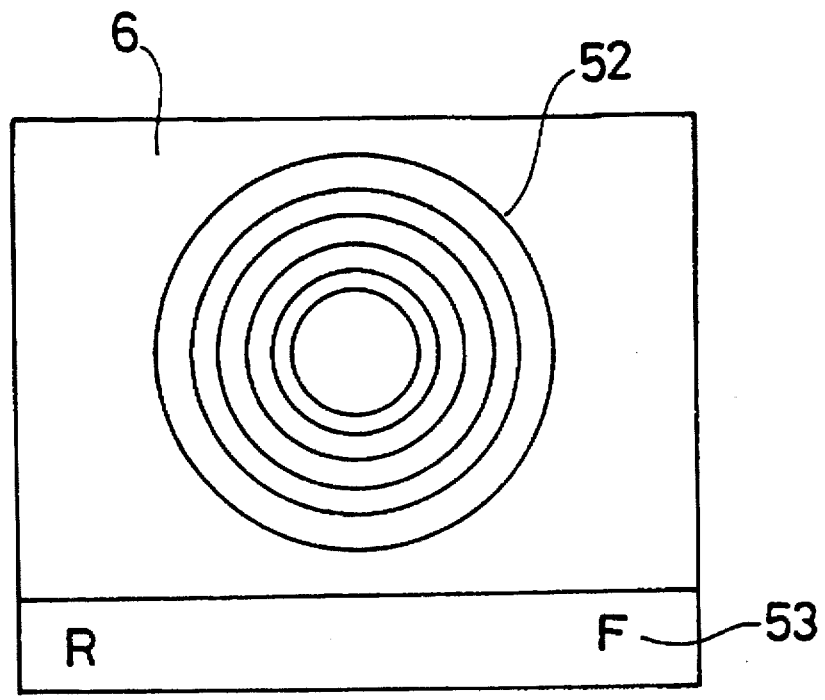
FIG. 6(a) shows a case where photographic mode information is displayed together with image data on the TV monitor.
Figure 6B:
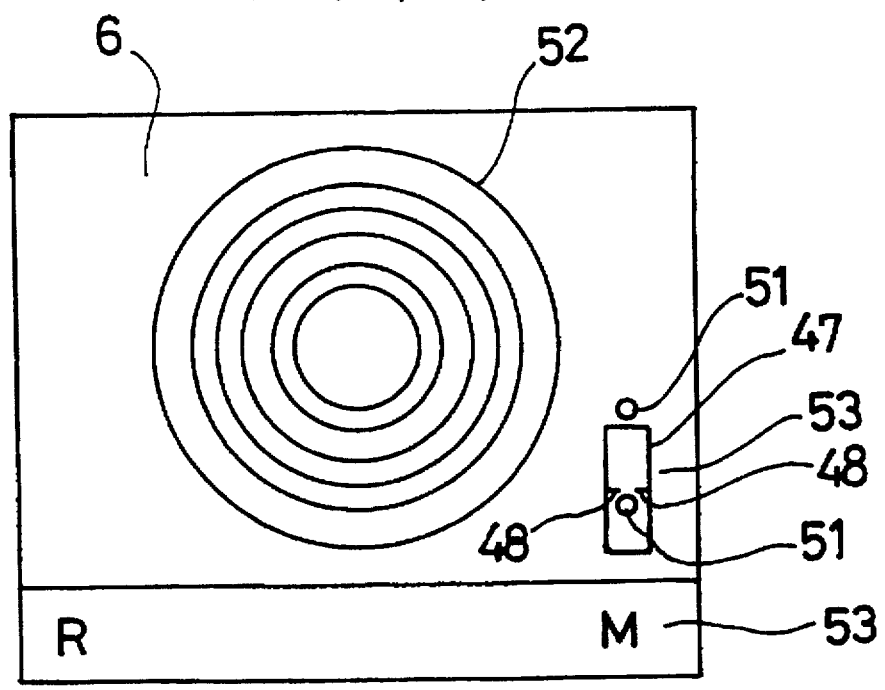
FIG. 6(b) shows a case where a positional relationship between the apparatus body and the subject's eye is displayed in the form of a diagram together with image data.

The image data and the pattern information generated by the pattern generator 28 are input to the analysis portion 32 via the image synthesizing device 31 and are temporarily stored therein. As shown in FIG. 6(a), ring image data 52 and photographic mode information 53 are correlatively stored in the analysis portion 32. These data and information are displayed on the monitor 6 as occasion demands. As shown in FIG. 6(a), the character "F" indicating the automatic (full automatic) photographic mode is displayed together with the ring image data 52 on the monitor 6. In order to indicate the photographic mode information 53, a positional relationship between the apparatus body 3 and the subject's eye may be additionally displayed in the form of a diagram as shown in FIG. 8(b). For instance, a rectangular diagram indicating the previous positional relationship of the apparatus body 3 to the identical subject's eye is displayed when observing an image of the eye photographed this time. If such a relationship therebetween is displayed as shown in FIG. 6(b), photography can be carried out under the same conditions. This is effective in examining the shape of the cornea of the subject's eye at regular intervals. In other words, if there is previous alignment data on the identical eye, since an alignment area can be determined based on the previous one, a comparison can be facilitated between the previous ring image data and the present one. In this embodiment, in order to indicate the photographic mode information 53, the positional relationship between the apparatus body 3 and the subject's eye is displayed in the form of the diagram. Instead, a difference between a position of the apparatus body 3 in forward and backward directions with respect to the subject's eye and a proper focal point may be displayed in the form of a numerical value and, at the same time, a position of the apparatus body 3 in up, down, right, left directions with respect to the subject's eye may be displayed in the form of variables of three-dimensional coordinate system.

The character "R" shown in FIG. 4(a) through FIG. 6(b) designates a right eye, the character "S" shown in FIGS. 5(a)–5(b) designates the semi-automatic photographic mode, and the character "M" shown in FIG. 6(b) designates the manual photographic mode.

In order to judge whether an analyzed image is reliable or not, a quantity of deviation from a normal state (i.e., from a state in which there is neither deviation in alignment nor eclipse of a ring image caused by eyelids or eyelashes) may be qualitatively or quantitatively displayed using a bar meter or the like. Further, when the identical eye is photographed plural times, reliable data may be displayed together with a ring image so that, based on the reliable data, the most reliable image to be recorded in a recording device can be selected from several frame memories. The provision of an automatic selection mode in the apparatus makes it possible to record the most reliable ring image data, thus enabling the oculist to make a minute analysis based on the optimum image data.

What is claimed is:

1. A corneal shape measuring apparatus for measuring a corneal shape in such a way that a reflection image from a cornea is recorded as image data and then the image data is analyzed, said apparatus including:

an automatic photographic mode in which a subject's eye is automatically photographed when a position of an apparatus body in up, down, right, and left directions with respect to the subject's eye is within a predetermined range and a position of said apparatus body in forward and backward directions with respect to the subject's eye is within a predetermined range;

a semi-automatic photographic mode in which the subject's eye is photographed when a position of said apparatus body in up, down, right, and left directions with respect to the subject's eye is within a predetermined range and a position of said apparatus body in forward and backward directions with respect to the subject's eye is within a predetermined range and, at the same time, a photography switch is operated; and a manual photographic mode in which the subject's eye is photographed when said photography switch is operated regardless of a position of said apparatus body with respect to the subject's eye.

2. A corneal shape measuring apparatus as recited in claim 1, wherein photographic mode information corresponding to recorded image data is recorded and displayed together with the image data.

3. A corneal shape measuring apparatus as recited in claim 1, wherein the position, determined when the image data is obtained, of said apparatus body in up, down, right, and left directions with respect to the subject's eye and the position, determined when the image data is obtained, of said apparatus body in forward and backward directions with respect to the subject's eye are stored correspondingly to the image data or analysis data.

4. A corneal shape measuring apparatus for measuring a corneal shape in such a way that a reflection image from a cornea is recorded as image data and then the image data is analyzed, said apparatus including:

index projecting means for projecting an index onto a subject's eye in order to detect a position of an apparatus body in up, down, right, and left directions with respect to a subject's eye and a position of said apparatus body in forward and backward directions with respect to the subject's eye;

an automatic photographic mode in which the subject's eye is automatically photographed when a position of said apparatus body in up, down, right, and left directions with respect to the subject's eye is within a predetermined range and a position of said apparatus body in forward and backward directions with respect to the subject's eye is within a predetermined range;

a semi-automatic photographic mode in which the subject's eye is photographed when a position of said apparatus body in up, down, right, and left directions with respect to the subject's eye is within a predetermined range and a position of said apparatus body in forward and backward directions with respect to the subject's eye is within a predetermined range and, at the same time, a photography switch is operated; and a manual photographic mode in which the subject's eye is photographed when said photography switch is operated regardless of a position of said apparatus body with respect to the subjects eye;

a positional relationship of said apparatus body to the subject's eye being stored correspondingly to recorded image data.

5. A corneal shape measuring apparatus as recited in claim 4, wherein photographic mode information corresponding to the recorded image data is recorded and displayed together with the image data.

6. A corneal shape measuring apparatus as recited in claim 5, wherein the positional relationship of said apparatus body to the subject's eye is displayed in the form of a diagram.

7. A corneal shape measuring apparatus as recited in claim 6, wherein said diagram comprises a rectangular frame, a focusing line, and a pair of index images.

8. A corneal shape measuring apparatus as recited in claim 7, wherein a lateral width of said rectangular frame in the automatic photographic mode is different from that in the semi-automatic photographic mode, the lateral width of said rectangular frame in the semi-automatic photographic mode being narrower than that in the automatic photographic mode.

9. A corneal shape measuring apparatus as recited in claim 8, wherein a direction for focusing in which said apparatus body is moved with respect to the subject's eye is indicated by an arrow.

10. A corneal shape measuring apparatus as recited in claim 6, wherein a diagram indicating a previous positional relationship of said apparatus body to the identical subject's eye is displayed when an image of the subject's eye photographed at present is observed.

11. A corneal shape measuring apparatus for measuring a corneal shape in such a way that a reflection image from a cornea is recorded as image data and then the image data is analyzed, said apparatus including:

a semi-automatic photographic mode in which a subject's eye is photographed when a position of an apparatus body in up, down, right, and left directions with respect to the subject's eye is within a predetermined range and a position of said apparatus body in forward and backward directions with respect to the subject's eye is within a predetermined range and, at the same time, a photography switch is operated whereas the subject's eye is not photographed when either a position of said apparatus body in up, down, right, and left directions with respect to the subject's eye or a position of said apparatus body in forward and backward directions with respect to the subject's eye is outside a predetermined range even if said photography switch is operated.

12. A corneal shape measuring apparatus as recited in claim 11, said apparatus further including an automatic photographic mode in which the subject's eye is automatically photographed when a position of said apparatus body in up, down, right, and left directions with respect to the subject's eye is within a predetermined range and a position of said apparatus body in forward and backward directions with respect to the subject's eye is within a predetermined range.

13. A corneal shape measuring apparatus as recited in claim 11, said apparatus further including a manual photographic mode in which the subject's eye is photographed when said photography switch is operated regardless of a position of said apparatus body with respect to the subject's eye.

* * * * *